United States Patent [19]
Robinson et al.

[11] 3,946,053
[45] Mar. 23, 1976

[54] HYDROCARBYL HYDROGEN PHOSPHATE SALTS OF AMINO-AMIDES

[75] Inventors: Franklin H. Robinson, N. Brunswick; Marvin S. Rakow, E. Brunswick; Ernest Jamieson, Highland Park, all of N.J.

[73] Assignee: Cities Service Oil Company, Tulsa, Okla.

[22] Filed: Sept. 30, 1970

[21] Appl. No.: 77,040

[52] U.S. Cl. .......... 260/404.5; 44/63; 44/66; 44/71; 260/501.19; 260/558 A; 260/561 A; 260 309.6
[51] Int. Cl.² ................................. C11C 3/00
[58] Field of Search ........ 260/404.5, 558 R, 561 N, 260/561 P; 44/66, 76, 72

[56] References Cited
UNITED STATES PATENTS

| | | | |
|---|---|---|---|
| 3,256,073 | 6/1966 | Hess | 44/66 |
| 3,303,007 | 2/1967 | Mueller | 44/66 |
| 3,427,141 | 2/1969 | Miller et al. | 44/66 |
| 3,623,851 | 11/1951 | Konig et al. | 44/66 |
| 3,647,694 | 3/1972 | Swanson et al. | 44/66 |
| 3,655,351 | 4/1972 | Jamieson | 260/404.5 |
| 3,658,493 | 4/1972 | Hollyday, Jr. | 44/66 |

*Primary Examiner*—Glennon H. Hollrah
*Attorney, Agent, or Firm*—John W. Carpenter

[57] ABSTRACT

Hydrocarbyl acid phosphate salts of polyamides having at least one amino group and hydrocarbon fuel compositions containing same. The salts are formed by neutralizing with a hydrocarbyl acid phosphate at least 10% of the amino groups of a polyamide containing from about 2 to about 6 amide groups and at least one amino group. Hydrocarbon fuel compositions containing these salts exhibit desirable properties such as enhanced carburetor detergency and carburetor anti-icing characteristics, improved water tolerance, excellent rust inhibition, and cleaner engine operation while engines operated thereon exhibit reduced hydrocarbon content in the exhaust.

8 Claims, No Drawings

HYDROCARBYL HYDROGEN PHOSPHATE SALTS OF AMINO-AMIDES

BACKGROUND OF THE INVENTION

Normally liquid hydrocarbon fuels often require additives to improve their performance characteristics. Thus, in fuels such as gasoline, diesel fuel and jet fuel, various additives are employed to assist in maintaining cleanliness in the carburetor and fuel intake system and to prevent carburetor icing as well as to inhibit rust. The additives vary in effectiveness, and it is often necessary to use a number of additives in a single composition.

Many additives for hydrocarbon fuels are only marginally soluble in hydrocarbons. Furthermore, they are often employed in concentrations that approach their limits of solubility. As a result, hydrocarbon compositions containing such additives often exhibit poor stability and, as a result, on standing the additive may precipitate.

In addition, many additives for hydrocarbon fuels have poor water tolerance. When fuel compositions containing such additives come in contact with water as, for example, in storage tanks, water enters the hydrocarbon phase. This is particularly deleterious in jet fuels. The temperatures at high altitudes where jet aircraft operate are well below freezing. Hence, water in the fuel crystallizes and plugs fuel filters, thereby cutting off the flow of fuel to the engines. To combat this, fuel tank heaters and additives to prevent ice formation are employed.

A serious problem relating to internal combustion engines is environmental pollution as, for example, air pollution by exhaust emissions from internal combustion engines. A component of the exhaust from internal combustion engines is unburned hydrocarbons. Various methods have been used to reduce the hydrocarbons in engine exhausts, for example, catalytic mufflers and positive crank case ventilation systems.

SUMMARY OF THE INVENTION

Desirable properties such as carburetor detergency, good carburetor anti-icing characteristics and good rust inhibiting properties are imparted to normally liquid hydrocarbon fuels by the incorporation therein of hydrocarbon fuel-soluble organic compounds containing at least two amide linkages. A particularly efficacious type of compound of this class is compounds containing at least two amide linkages and having in addition at least one free amino group. It has been found that when these polyamides containing at least one free amino group are converted to the hydrocarbyl hydrogen phosphate salts, incorporation thereof into normally liquid hydrocarbon fuels not only favors improved carburetor detergency, carburetor anti-icing, and rust inhibiting properties but also results in other desirable properties. For example, hydrocarbon fuels containing hydrocarbyl hydrogen phosphate salts of polyamides having at least one amino group also have excellent stability and water tolerance and, in addition, engines operated thereon are characterized by reduced hydrocarbon emissions in the exhaust.

It is therefore an object of this invention to provide additives which, when incorporated in normally liquid hydrocarbon fuels, impart desirable properties thereto.

It is another object of this invention to provide additives which are readily soluble in normally liquid hydrocarbon fuels to produce stable solutions.

Yet another object of this invention is to provide normally liquid hydrocarbon fuel compositions having enhanced carburetor and fuel intake system detergency properties as well as superior carburetor anti-icing characteristics.

It is still another object of this invention to provide normally liquid hydrocarbon fuel compositions having improved water tolerance and rust inhibiting properties.

Yet another object of this invention is to provide normally liquid hydrocarbon fuel compositions which are characterized by reduced hydrocarbon content in the exhaust of internal combustion engines operated thereon.

Still other objects will appear hereinafter.

The foregoing objects are attained in accordance with this invention. In general, this invention comprises a hydrocarbyl hydrogen phosphate salt of a compound having the general formula

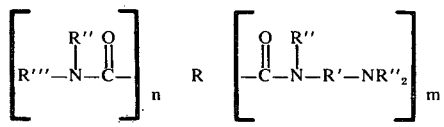

wherein $m$ is at least 1 and the sum of $n$ plus $m$ is from 2 to about 6, R is a multivalent hydrocarbon group of about 2 to about 52 carbons, $R'$ is a hydrocarbylene group of about 2 to about 12 carbons, $R''$ is selected from the group consisting of hydrogen and hydrocarbyl groups of about 1 to about 30 carbons, $R'''$ is a hydrocarbyl group of from about 2 to about 12 carbons, and at least 10% of the amino groups contained therein are converted to the hydrocarbyl hydrogen phosphate salt; and normally liquid hydrocarbon fuel compositions comprising a major proportion of a normally liquid hydrocarbon fuel and a minor proportion of the above additive.

Normally liquid hydrocarbon fuel compositions containing the additive compounds of this invention exhibit such desirable properties as enhanced carburetor and fuel intake system detergency properties as well as superior carburetor anti-icing characteristics. In addition, hydrocarbon fuel compositions containing our additives have good water tolerance which favors dry fuel, and they also have good rust inhibiting properties. A particularly favorable aspect of hydrocarbon fuel compositions containing the additive compounds of this invention is that internal combustion engines operated thereon exhibit markedly reduced hydrocarbon emissions in the exhaust. Furthermore, the good solubility of the additives of this invention in liquid hydrocarbon fuels ensures stability with little tendency toward gum formation. Another advantage of our additives is their ability to impart desirable properties to liquid hydrocarbon fuels when used at low concentrations which makes them economically attractive. Other advantages of this invention will be apparent from the following description.

DESCRIPTION OF THE PREFERRED EMBODIMENTS

The normally liquid hydrocarbon fuel compositions of this invention are prepared by incorporating into a major proportion of a normally liquid hydrocarbon fuel a minor proportion of an additive which is a hydrocarbon fuel-soluble organic compound containing at least two amide linkages. The additives useful in the present invention have the following general structures:

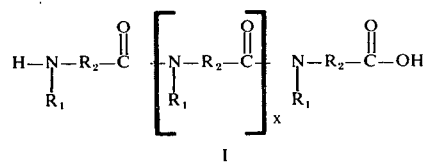

I

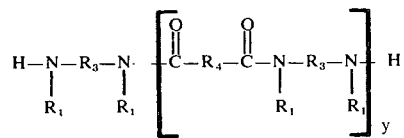

II

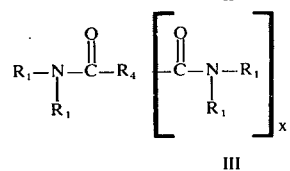

III wherein $R_1$ is hydrogen or a hydrocarbyl group of about 1 to about 30 carbons and preferably about 5 to about 25 carbons, e.g., an alkyl group, an aryl group, an aralkyl group, an alkaryl group, a cycloparaffin group, a cycloolefin group, or an aliphatic olefin group; $R_2$, $R_3$ and $R_4$ are polyvalent hydrocarbyl groups of about 2 to about 65 carbons and preferably about 3 to about 55 carbons, e.g., polyvalent aryl groups or olefinically saturated or unsaturated polyvalent alkyl groups, aralkyl groups, alkaryl groups, and naphthyl groups; $x$ is equal to or greater than one; and $y$ is such that the total number of amide linkages in the molecule is two or more. One or more hydrogens on hydrocarbyl groups $R_1$, $R_2$, $R_3$ and $R_4$ may be replaced by a heterocyclic group such as an imidazolyl group or by a functional group such as halide, hydroxyl, carboxyl, carbonyl, ester, mercaptyl, amino, substituted amino, or amide. $R_1$, $R_2$, $R_3$ or $R_4$ may be the same or different whenever they occur more than once in any one molecule. $R_3$ and $R_4$ may be the same or different in compounds represented by structure II. When $x$ is greater than 1 in compounds represented by structure III, the portion of the molecule within brackets may be attached to the same or different carbons in $R_4$.

Polyamides of the type represented by structure I may be prepared, for example, by condensing amino acids with one another through their respective amino and carboxyl groups. Polyamides of the type represented by structure II may be prepared, for example, by condensing dicarboxylic acids with diamines. Polyamides of the type represented by structure III may be prepared by condensing a polycarboxylic acid with ammonia or an amine. The amine may be selected from primary and secondary amines as well as compounds containing two or more amino groups.

Another class of amines that finds use in the practice of this invention is aminoalkyl substituted imidazolines of the general structure:

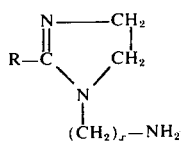

wherein $x$ is 1 to 8 and R is a hydrocarbyl group. When this class of amine is condensed with, for example, a dicarboxylic acid, the following type of diamide is produced:

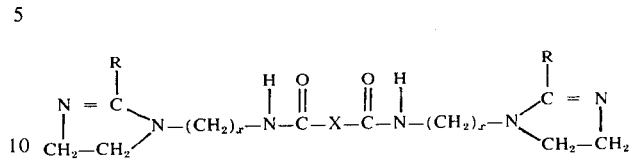

wherein X represents the non-carboxyl portion of the dicarboxylic acid.

It has been found that a particularly satisfactory class of amines is derived from 1,3-propylenediamine. Of these, N-(10-phenylstearyl)-1,3-propylenediamine and N-tallowyl-1,3-propylenediamine are especially efficacious. When a 1,3-propylenediamine is condensed with a dicarboxylic acid, in addition to diamide, some low molecular weight polyamide-type polymer of about 2 to 15 repeating units may be formed. It is also possible that the free amino groups of the diamide may react with the carbonyl oxygens of the amide groups to split out water and cyclize to form a tetrahydropyrimidine.

In addition to the dicarboxylic acids used to form amides represented by structure III when $x$ is 1, acids containing three, four or more carboxyl groups may be converted to amides and used successfully in the practice of this invention. An example is a trimer acid designated as Empol 1040 and which is manufactured by Emery Industries, Inc. This is the trimer of a polyunsaturated $C_{18}$ monocarboxylic fatty acid, being a $C_{54}$ tricarboxylic acid.

In addition to forming a polyamide by condensing a specific amine with a specific polycarboxylic acid, it is possible to condense mixtures of amines with mixtures of acids. An example of a useful mixture of acids is Empol 1022 which is comprised of about three parts of the dimer and about one part of the trimer of a polyunsaturated $C_{18}$ monocarboxylic fatty acid. An example of a suitable mixture of amines is two parts of 10-phenylstearylamine and one part of N-(10-phenylstearyl)-1,3-propylenediamine.

The polyamides of this invention may be prepared by adding one mole of the amine to each equivalent of the polycarboxylic acid in a suitable solvent and heating the mixture. Water formed as a by-product of the condensation reaction is removed from the reaction mixture, for example by azeotropic distillation. It is convenient when using an aromatic solvent such as toluene or xylene to employ a water separator to collect the by-product water. On completion of the reaction, removal of the solvent as, for example, by distillation leaves the polyamide.

The preferred normally liquid hydrocarbon fuel compositions of this invention are prepared by incorporating into a major proportion of a normally liquid hydrocarbon fuel a minor proportion of an additive which is basically a hydrocarbyl hydrogen phosphate salt of a polyamide having at least 1 amino group. Examples of normally liquid hydrocarbon fuels that have desirable properties imparted thereto by the additives of this invention are gasoline, jet fuel, and diesel fuel.

The novel additives of this invention are prepared by reacting a hydrocarbyl hydrogen phosphate with a polyamide containing from 2 to about 6 amide groups and at least 1 amino group whereby at least about 10% of the amino groups are converted to the hydrocarbyl hydrogen phosphate salt. The polyamides are prepared by condensing a polycarboxylic acid having from 2 to about 6 carboxyl groups with an amine or amines to convert each carboxyl group to the corresponding N-substituted amide group. It is critical that at least one N-substituted amide group in every molecule contain an amino group on the substituent. Thus at least one carboxyl group of the polycarboxylic acid must be condensed with a polyamine, preferably a diamine, while the remainder of the carboxyl groups may be condensed with either a monoamine or a polyamine. However, it is preferred that each carboxyl group be condensed with a diamine. The preferred acids are dicarboxylic acids. Hence the preferred polyamides are diamino-diamides having the general formula

wherein R is a hydrocarbylene group of about 2 to about 52 carbons and preferably about 4 to about 34 carbons, R' is a hydrocarbylene group of about 2 to about 12 carbons and preferably about 2 to about 6 carbons, and R'' is selected from the group consisting of hydrogen and hydrocarbyl groups of about 1 to about 30 carbons and preferably about 3 to about 24 carbons.

The hydrocarbyl hydrogen phosphate which is reacted with the polyamide containing one or more amino groups to form the salt is preferably a hydrocarbyl hydrogen orthophosphate. The hydrocarbyl hydrogen orthophosphate may be a dihydrocarbyl hydrogen orthophosphate, a hydrocarbyl dihydrogen orthophosphate, or preferably a mixture of a dihydrocarbyl hydrogen orthophosphate and a hydrocarbyl dihydrogen orthophosphate. The hydrocarbyl portions contain from about 1 to about 15 carbons and preferably from about 3 to about 10 carbons. In the case of dihydrocarbyl hydrogen orthophosphates and mixtures of dihydrocarbyl hydrogen orthophosphates and hydrocarbyl dihydrogen orthophosphates, the hydrocarbyl groups may be the same or different. The hydrocarbyl portions may be aliphatic, aromatic, or naphthenic or they may contain various mixtures of aliphatic, aromatic and naphthenic segments. Aliphatic and naphthenic segments may be either saturated or unsaturated. The ratio of hydrocarbyl hydrogen orthophosphate to the polyamide containing one or more amino groups is such that at least about 10% of the amino groups are converted to the hydrocarbyl hydrogen orthophosphate salt. While about 10% to about 100% of the amino groups may be converted to the hydrocarbyl hydrogen orthophosphate salt, it is preferred that about 50% to about 90% of the amino groups be converted to the salt since the presence of some free amino groups is usually desirable. However, an excess of hydrocarbyl hydrogen orthophosphate may be present in the case where 100% of the amino groups are converted to the salt.

As stated above, the polyamide containing from 2 to about 6 amide groups and at least 1 amino group has the general formula

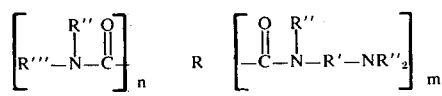

wherein R is a multivalent hydrocarbon group of about 2 to about 52, and preferably about 4 to about 34, carbons, and $m$ is at least 1 and the sum of $n$ plus $m$ is from 2 to about 6. The polycarboxylic acid from which the polyamide is made therefore has the general formula

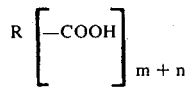

wherein R is a multivalent hydrocarbon group of about 2 to about 52 carbons and preferably about 4 to about 34 carbons. R may be aliphatic, aromatic or naphthenic, or it may contain various mixtures of aliphatic, aromatic and naphthenic segments. Aliphatic and naphthenic segments may be either saturated or unsaturated. While the sum of $m$ plus $n$ may be from 2 to about 6, it is preferred that the sum of $m$ plus $n$ be 2, i.e., a dicarboxylic acid. Examples of suitable polycarboxylic acids are succinic acid; glutaric acid; adipic acid; terephthalic acid; 1,4-cyclohexanedicarboxylic acid; pyromellitic acid; 1,18-dicarboxyoctadecane; and trimer acid which is the trimer of a polyunsaturated $C_{18}$ monocarboxylic fatty acid, being a $C_{54}$ tricarboxylic acid of uncertain structure. The preferred polycarboxylic acid is a dimer acid produced by the dimerization of a polyunsaturated $C_{18}$ monocarboxylic fatty acid to produce an unsaturated $C_{36}$ dicarboxylic acid whose exact structure is not known with certainty. Such a dimer acid is produced by General Mills under the trade name of Versadyme 216.

The amine which is condensed with the polycarboxylic acid to form the polyamide is selected from the group consisting of monoamines and polyamines, preferably diamines, having the general formulas

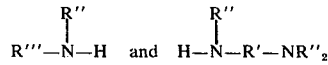

wherein R' is a hydrocarbylene group of about 2 to about 12 carbons and preferably about 2 to about 6 carbons, R'' is selected from the group consisting of hydrogen and hydrocarbyl groups of about 1 to about 30 carbons and preferably about 3 to about 24 carbons, and R''' is a hydrocarbyl group of about 2 to about 12 carbons and preferably about 2 to about 6 carbons. R', R''', and R'' when it is a hydrocarbyl group may be aliphatic, aromatic or naphthenic or they may contain various mixtures of aliphatic, naphthenic and aromatic segments. Aliphatic and naphthenic segments may be either saturated or unsaturated. Examples of suitable monoamines are diethylamine, dodecylamine, cyclohexylamine, methylbutylamine and propylamine. Examples of suitable diamines are ethylenediamine; propylenediamine; 1,12-diaminododecane; hexamethylenediamine; N-methyl-N'-propyl-1,3-propylenediamine; N,N-dibutylethylenediamine; 1,4-diaminohexane; N-oleyl-1,3-propylenediamine; N-cyclohexylethylenediamine; and N-(10-phenylstearyl)-1,3-propylenediamine. The preferred amine is N-tallowyl-1,3-propylenediamine.

Examples of hydrocarbyl hydrogen phosphates are triethyl hydrogen pyrophosphate, methylphenyl dihydrogen pyrophosphate, cyclohexyl dihydrogen orthophosphate, diphenyl hydrogen orthophosphate, methyldecyl hydrogen orthophosphate, pentadecyl dihydrogen orthophosphate, dipropyl hydrogen orthophosphate, heptyl dihydrogen orthophosphate, isooctyl dihydrogen orthophosphate, and diisooctyl hydrogen orthophosphate. The preferred hydrocarbyl hydrogen phosphate is a mixture of isooctyl dihydrogen orthophosphate and diisooctyl hydrogen orthophosphate.

In order that the additive of our invention have the necessary solubility in hydrocarbon fuels, it is necessary that the polyamide containing from 2 to about 6 amide groups and at least one amino group contain about 24 to about 100, and preferably about 30 to about 90, carbons. Since the preferred acid for amide formation is dimer acid, the preferred amine is N-tallowyl-1,3-propylenediamine, and the preferred hydrocarbyl hydrogen phosphate for salt formation is a mixture of isooctyl dihydrogen orthophosphate and diisooctyl hydrogen orthophosphate, the preferred additive of our invention is a mixture of isooctyl dihydrogen orthophosphate and diisooctyl hydrogen orthophosphate salts of the diamide obtained by condensing one mole of dimer acid with 2 moles of N-tallowyl-1,3-propylenediamine. It will be understood that when the dimer acid condenses with the diamine to form the diamino-diamide, either amino group may condense with a carboxyl group and the product is therefore a mixture of the following isomers

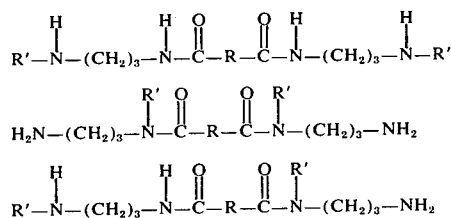

wherein R is the $C_{34}$ hydrocarbylene portion of the dimer acid and R' is a tallowyl group. The ratio of the mixture of isooctyl hydrogen orthophosphates to the diamino-diamide to form our preferred additive is such as to convert from about 10% to about 100%, and preferably about 50% to about 90%, of the amino groups of the diamino-diamide to the corresponding isooctyl hydrogen orthophosphate salts. In the case where 100% of the amino groups are converted to the salt, it is contemplated that an excess of the mixture of isooctyl hydrogen orthophosphates may be present.

A particularly advantageous method of incorporating the additive of this invention into a normally liquid hydrocarbon fuel is to form a "cocktail" of the additive with other ingredients which, for example, enhance the ease of solution of the additive in the fuel and the handling characteristics of the additive itself. An especially desirable "cocktail" contains 45 weight percent of the preferred additive of this invention, the additive being prepared by reacting about 3 parts by weight of the condensation product of 1 mole of dimer acid and 2 moles of N-tallowyl-1,3-propylenediamine with about 1 part by weight of a mixture of about 65 weight percent diisooctyl hydrogen orthophosphate and about 35 weight percent of isooctyl dihydrogen orthophosphate. Thus about 80–90% of the amino groups of the diamino-diamide are neutralized by the mixture of isooctyl hydrogen orthophosphates. The remainder of the "cocktail" comprises 48.6 weight percent toluene, 4.5 weight percent methanol, and 1.9 weight percent of a demulsifying agent, advantageously DS-415 manufactured by Petrolite Corporation.

"Cocktails" of additives of this invention with other ingredients which, for example, enhance the solubility of the additive will vary depending on a number of factors. The concentration of the additive in the "cocktail" will generally be as high as possible commensurate with ready solubility of the "cocktail" in the hydrocarbon fuel. Generally, the concentration of additive in the "cocktail" is about 40–60 weight percent. The other components of the "cocktail" will generally be solvents or mixtures of solvents that readily dissolve the additive and which are miscible with the hydrocarbon fuel, as well as materials such as demulsifying agents.

While the concentrations of the additives of this invention in hydrocarbon fuels may be varied over a broad range, hydrocarbon fuel compositions containing from about 1 to about 500 pounds of additive per thousand barrels (PTB) of the composition are generally used. However, hydrocarbon fuel compositions containing from about 4 to about 50 PTB of additive are preferred.

In the case of the "cocktail" described above which contains 40–60 weight percent of an additive of this invention, its concentration in the normally liquid hydrocarbon fuel composition may vary from about 5 to about 1000, and preferably from about 10 to about 100, PTB of said "cocktail." When the normally liquid hydrocarbon fuel is gasoline, a particularly desirable gasoline composition contains about 13 to about 20 PTB of said "cocktail."

The efficacy of our additives in hydrocarbon fuel compositions is determined by subjecting the compositions to one or more of the following tests. The tests and their procedures are as follows:

CARBURETOR DETERGENCY TEST

Engine blow-by contaminants are generated in an engine and collected in a flask. At the end of the collection period the water phase is separated from the fuel phase, the latter being discarded. The water phase of the contaminants is used for the carburetor detergency evaluations.

The carburetor detergency test is run on a Cooperative Lubricants Research (CLR) engine, a single cylinder research engine manufactured by Laboratory Equipment Company. The contaminants are injected into the carburetor throttle body of a CLR engine running with a rich mixture and on which the throttle plate has been removed and a 200 mesh stainless steel specimen screen installed at the entrance to the intake manifold. The amount of deposits accumulated on the screen after 3 hours of engine operation indicates the detergency performance of the fuel. Experimental fuels and reference fuels are tested with the same batch of contaminants.

At the conclusion of the 3 hour run, the 200 mesh screen is removed and evaluated for contaminant accumulation. The reflectance of the screen, determined by means of a reflectance meter, is a measure of the amount of deposits accumulated on the screen. The higher the reflectance, the cleaner the screen, i.e., the lower the accumulation of deposits.

The effectiveness of an additive is represented as the ratio, expressed as a percentage, of the average screen reflectance for the fuel containing the additive to the average screen reflectance for a reference fuel containing a commercially available carburetor detergent additive at a concentration of 15 pounds per thousand barrels (PTB). Thus an experimental additive that equals the performance of the reference fuel will have an effectiveness of 100%, and an experimental additive that performs at a lower level than the reference fuel will have an effectiveness of less than 100%, and an experimental additive that performs at a higher level than the reference fuel will have an effectiveness of greater than 100%.

CARBURETOR ANTI-ICING TEST

The test is run on a CLR single cylinder engine coupled to a speed control dynamometer. The engine is fitted with a special, thermally-isolated carburetor with external float bowls; no idle fuel system is used. The carburetor has an adjustable main jet and the throttle body is constructed of glass or clear plastic so icing can be confirmed by visual inspection. A temperature and humidity control system supplies inlet air to the carburetor at the desired conditions and also to a glass or clear plastic box enclosing the carburetor.

All anti-icing additives are evaluated in a blended base fuel composed of 25 volume percent of ASTM isooctane and 75 volume percent of precipitation naphtha and containing 1.5 ml./gallon of tetraethyl lead. Also present are a scavenger, metal deactivator, and an anti-oxidant. A non-icing purge fuel consisting of the base fuel containing 5.5% of isopropyl alcohol is used in the test. The anti-icing properties of fuel compositions containing additives of this invention are compared to those of the base fuel containing no anti-icing additive.

Ice formation on the throttle plate of the carburetor is measured by an increase in manifold vacuum caused by a choking of the engine by the ice formation. The time in seconds for the manifold vacuum to increase 1.5 and 2.0 inches of mercury are recorded as time to ice with the fuel which is being evaluated. An increase in manifold vacuum of 1.5 inches of mercury is defined as trace ice and an increase in manifold vacuum of 2.0 inches of mercury is defined as severe ice.

Engine operating conditions are set so as to cause a reference fuel, i.e., a base fuel containing a reference anti-icing additive, to ice sufficiently to cause a 2.0 inch manifold vacuum increase in 40 to 50 seconds. When these conditions are set, the base fuel containing no anti-icing additives will ice to the same extent in 18 to 20 seconds. Once these operating conditions have been achieved, the anti-icing characteristics of base fuel containing the experimental additives can be evaluated.

In running the test on a fuel composition containing an experimental additive, once ice severe enough to raise the manifold vacuum 2.0 inches of mercury has formed, the carburetor is switched to the purge fuel which removes the ice. After 50 seconds to allow for ice removal and engine stabilization, the carburetor is switched back to the experimental fuel. The above procedure is repeated until five runs on the experimental fuel have been made, the times for manifold vacuum increases of 1.5 to 2.0 inches of mercury being noted. The times of the five runs are then averaged for each manifold vacuum increase. Either a base fuel or a reference fuel is run after every two experimental additive runs.

WATER TOLERANCE TEST

Into an 8 oz. bottle are poured 100 ml. of the fuel composition to be tested plus 20 ml. of water of a given pH. The bottle is capped and hand-shaken with an up-down motion for 2.5 minutes, approximately 180 to 200 times. The mixture is stored in the dark on a vibration-free table for 24 hours and is then rated. The interface is rated numerically according to accumulations of skin, dirt, bubbles and emulsion, and the numbers range from 0 to 7. A rating of 0 denotes a clean break at the interface with no accumulations of any kind. A rating of 7 denotes that the water phase is occupied completely by emulsion. Various degrees of accumulations at the interface are thus assigned numerical values ranging from 0 for no accumulation to 7 for the poorest rating. Finer variations in the ratings may be denoted by + and − signs after the numerical rating. Thus a rating of 2− is slightly better than a rating of 2 while a rating of 5+ is slightly poorer than a rating of 5. In addition, both the fuel phase and the water phase are rated for clarity as follows:

C — very clear, no haze
SH — slightly hazy
H — hazy
VH — very hazy
E — emulsion.

Passing ratings for a fuel composition are an interface rating of 0 to 2 and fuel and water phase clarity rating of C.

MULTIPLE CONTACT EMULSION TEST

In an 8 oz. narrow-necked bottle are placed 100 ml. of the fuel to be tested and 10 ml. of water of a given pH. The mixture is shaken by hand for 2.5 minutes. The bottle is stored in an upright position in the dark and at the end of 24 hours the appearance of the fuel layer, oil-water interface and water layer are noted. The fuel layer is siphoned off and replaced with a fresh 100 ml. sample of the fuel to be tested. This procedure is repeated for a total of 10 times or until such time as the water layer is completely emulsified after the 24 hour setting period. At the end of each 24 hour period, the sample is rated according to a scale ranging from 0 to 11. A rating of 0 denotes clean separation of fuel and water while the poorest rating of 11 indicates a completely solid emulsion. As in the case of the water tolerance test described above, plus and minus signs are applied to the numerical ratings to indicate finer variations therein.

RUST TEST

A 350 ml. sample of the normally liquid hydrocarbon fuel composition to be tested is extracted by shaking with 35 ml. of distilled water. The water phase is then discarded. Into a beaker are placed 30 ml. of synthetic sea water and 300 ml. of the extracted normally liquid hydrocarbon fuel composition to be tested. The stirred mixture is heated to 100°F. A steel test specimen is inserted into the stirred, heated mixture and the mixture is stirred at 100°F for 20 hours. The steel specimen is then removed, allowed to drain and then washed with precipitation naphtha or isooctane. The percent of the surface of the steel test specimen that is covered by rust is determined.

EQUILIBRIUM HYDROCARBON EMISSION TEST

The test is run using a CLR single cylinder test engine. The engine is clean at the beginning of the test and has no combustion chamber deposits. By means of a Beckman flame ionization detector (FID), the amount of hydrocarbon emissions in the exhaust at the start of the test is determined for the fuel being tested. The engine is run on this fuel until equilibrium is reached as evidenced by no change in the amount of hydrocarbons in the exhaust. The increase in hydrocarbon emissions at equilibrium over the initial hydrocarbon emissions is recorded and expressed in parts per million (p.p.m.).

CLEAN-UP HYDROCARBON EMISSION TEST

The test is run on a clean CLR single cylinder test engine having no combustion chamber deposits. The initial fuel is a base fuel containing 3 ml. of TEL/gallon. Using the procedure described above, the engine is run on the base fuel until equilibrium is reached. The increase in hydrocarbon emissions at equilibrium relative to the initial hydrocarbon emissions in the exhaust is determined (FID) and expressed in p.p.m. The engine is then switched to a fuel containing the additive of this invention and run for another 75 hours. At this time the amount of hydrocarbons in the exhaust is again determined and the change relative to the equilibrium hydrocarbon emissions recorded in p.p.m.

The following specific examples will serve to better illustrate our invention.

EXAMPLE I

To a solution of 147.5 g. (0.25 mole) of Versadyme 216 dimer acid in 200 ml. of toluene are added 178.0 g. (0.5 mole) of N-tallowyl-1,3-propylenediamine. The reaction mixture, in a flask fitted with a stirrer, a Dean-Stark trap and a reflux condenser, is stirred while heated under reflux for 13.5 hours. At the end of this time, 9.0 ml. of water, the theoretical amount for formation of the mixture of isomeric diamino-diamides, have been collected in the Dean-Stark trap. The solvent is removed by distillation under reduced pressure to yield 319.0 g. of the mixture of isomeric diamino-diamides having a basic nitrogen content of 3.06 weight percent.

To 100 g. of the mixture of isomeric diaminodiamides are added 36.2 g. of an approximately equimolar mixture of diisooctyl hydrogen orthophosphate and isooctyl dihydrogen orthophosphate containing a small amount of orthophosphoric acid and having an equivalent weight of 184. The mixture of isooctyl hydrogen orthophosphates is sufficient to react with 90% of the amino groups of the diamino-diamides to form the corresponding salts. To the reaction mixture are added 5.68 g. of Petrolite DS-415, a demulsifying agent manufactured by Petrolite Corporation. The mixture is stirred and the temperature rises to 52°C. A portion of this mixture is mixed with toluene and methanol to form a "cocktail" having the composition:

| Ingredients | Weight Percent |
| --- | --- |
| Isooctyl hydrogen orthophosphate salts of diamino-diamides | 45.0 |
| Petrolite DS-415 demulsifying agent | 1.9 |
| Toluene | 48.6 |
| Methanol | 4.5 |

EXAMPLE II

Gasoline compositions are prepared by dissolving various amounts of a "cocktail" having the composition of that described in Example I in a base gasoline containing 3 ml. of TEL/gal. and the compositions are subjected to the carburetor detergency test. For comparison purposes, a base leaded gasoline containing no other additive than 3 ml. of TEL/gal. and leaded (3 ml. of TEL/gal.) gasoline compositions containing various levels of a commercially available mutli-functional additive, i.e., DMA-4 manufactured by the Du Pont Company and containing 80% of active ingredient and 20% kerosene, are also subjected to the carburetor detergency test. The active ingredient in DMA-4 is a hydrocarbyl hydrogen orthophosphate salt of an aliphatic monoamine. The make-up of each gasoline composition and its percent effectiveness as determined by the average screen reflectance are given in Table I. The gasoline composition containing 15 PTB of DMA-4 has been assigned an effectiveness of 100% and all results are relative to this reference. Each result is the average of a number of determinations.

TABLE I

| Additive | Concentration, PTB | % Effectiveness |
| --- | --- | --- |
| — | — | 64 |
| DMA-4 | 15.0 | 100 |
| DMA-4 | 22.5 | 109 |
| DMA-4 | 30.0 | 147 |
| Additive "Cocktail" | 13.0 | 200 |
| Additive "Cocktail" | 20.0 | 252 |
| Additive "Cocktail" | 33.0 | 289 |

It is seen from Table I that gasoline compositions containing a "cocktail" of an additive of this invention, said "cocktail" having the composition of that described in Example I, have excellent carburetor detergency properties.

EXAMPLE III

Fuel compositions are prepared by dissolving various amounts of a "cocktail" having the composition of that described in Example I in a high volatility fuel comprising a blend of isooctane and precipitation naphtha containing 1.5 ml. of TEL/gal. and the compositions are subjected to the carburetor anti-icing test. For comparison purposes, a base fuel containing no other additive than 1.5 ml. of TEL/gal. and base fuel compositions containing various levels of the commercial multi-functional additive DMA-4 are also subjected to the carburetor anti-icing test. The make-up of each fuel composition and its percent effectiveness are given in Table II. The percent effectiveness for each composition is determined by averaging the times for 1.5 inch and 2.0 inch manifold vacuum increases and comparing the average time to the average time for a fuel composition containing 15 PTB of DMA-4 which has been assigned an effectiveness of 100%.

TABLE II

| Additive | Concentration, PTB | % Effectiveness |
| --- | --- | --- |
| — | — | 52 |
| DMA-4 | 5.0 | 80 |
| DMA-4 | 10.0 | 90 |
| DMA-4 | 15.0 | 100 |
| Additive "Cocktail" | 13.0 | 80 |
| Additive "Cocktail" | 20.0 | 101 |
| Additive "Cocktail" | 27.0 | 113 |
| Additive "Cocktail" | 33.0 | 148 |

The data in Table II show that fuel compositions containing a "cocktail" of an additive of this invention have improved carburetor anti-icing properties compared to a base fuel and that they compare favorably to fuel compositions containing a commercially available additive.

EXAMPLE IV

Fuel compositions are prepared by dissolving various amounts of an additive "cocktail" having the composition of that described in Example I in isooctane and the compositions are subjected to the rust test. Also subjected to the rust test are a sample of isooctane containing no additive and a composition comprising isooctane containing 15 PTB of DMA-4. The make-up of each fuel composition and the results of the rust test are set forth in Table III.

TABLE III

| Additive | Concentration, PTB | % Rust |
| --- | --- | --- |
| — | — | 100 |
| DMA-4 | 15.0 | 62 |
| Additive "Cocktail" | 13.0 | 0 |
| Additive "Cocktail" | 20.0 | 0 |
| Additive "Cocktail" | 33.0 | 0 |

The data in Table III illustrate the excellent rust inhibiting properties imparted to a fuel composition by the incorporation therein of an additive of this invention.

EXAMPLE V

Gasoline compositions containing an additive "cocktail" having the composition of that described in Example I and gasoline compositions containing multi-functional additive DMA-4 are subjected to the water tolerance test using water of various pH. The make-up of each composition, the pH of the water used, and the results of the test are given in Table IV.

TABLE IV

| Additive | Concentration, PTB | pH of Water | Water Tolerance Ratings | | |
| --- | --- | --- | --- | --- | --- |
| | | | Gasoline Phase | Water Phase | Interface |
| DMA-4 | 15.0 | 6.0 | C | C | 0 |
| DMA-4 | 15.0 | 7.0 | C | C | 0 |
| DMA-4 | 15.0 | 9.0 | C | C | 0 |
| Additive "Cocktail" | 33.0 | 5.0 | C | C | 0+ |
| Additive "Cocktail" | 33.0 | 6.0 | C | C | 0 |
| Additive "Cocktail" | 33.0 | 9.0 | C | C | 0+ |

The data in Table IV show the excellent water tolerance of gasoline compositions containing a "cocktail" of an additive of this invention.

EXAMPLE VI

Gasoline compositions are prepared containing different levels of an additive "cocktail" having the same composition as that described in Example I, and the gasoline compositions are subjected to the multiple contact emulsion test using water of various pH levels. A gasoline composition containing multi-functional additive DMA-4 is also subjected to the test for comparison purposes. The make-up of each composition, the pH of the water used, and the interface rating after the tenth contact are shown in Table V.

TABLE V

| Additive | Concentration PTB | pH of Water | Interface Rating After 10th Contact |
| --- | --- | --- | --- |
| Additive "Cocktail" | 13.0 | 5.0 | 2+ |
| " | 13.0 | 6.0 | 2+ |
| " | 13.0 | 10.0 | 1+ |
| " | 27.0 | 5.0 | 2+ |
| " | 27.0 | 6.0 | 2+ |
| " | 27.0 | 10.0 | 2+ |
| DMA-4 | 15.0 | 5.0 | 3− |
| DMA-4 | 15.0 | 6.0 | 3− |
| DMA-4 | 15.0 | 10.0 | 3− |

From the results of the test as shown in Table V it is seen that gasoline compositions containing a "cocktail" of an additive of this invention have a water tolerance somewhat better than gasoline compositions containing the commercial additive.

EXAMPLE VII

A number of gasoline compositions are evaluated in a CLR single cylinder engine to determine the increase in hydrocarbon emissions at equilibrium relative to initial hydrocarbon emissions in a clean engine. As described above, a flame ionization detector (FID) is used to determine the initial hydrocarbon emissions in the exhaust of a clean CLR engine. The engine is run to equilibrium as indicated by a stabilization of the hydrocarbon emissions. The increase in hydrocarbon emissions at equilibrium, expressed in p.p.m., and the time to reach equilibrium are recorded. A gasoline composition is prepared by dissolving an additive "cocktail" having the composition of that described in Example I in a base gasoline composition containing 3 ml. of TEL/gal. and evaluated. For comparison, a base leaded gasoline containing no additive other than 3 ml. of TEL/gal. and a leaded (3 ml. of TEL/gal.) gasoline composition containing multi-functional additive DMA-4 are also evaluated in the test. Table VI shows the make-up of the gasoline compositions, the increase in hydrocarbon emissions in the exhaust at equilibrium, and the time to reach equilibrium.

TABLE VI

| Additive | Concentration PTB | Δ Hydrocarbon Emission at Equilibrium p.p.m. | Time to Equilibrium hrs. |
|---|---|---|---|
| — | — | +177 | 65 |
| DMA-4 | 15.0 | +185 | 65 |
| DMA-4 | 15.0 | +220 | 85 |
| Additive "Cocktail" | 20.0 | +2 | 100+ |
| Additive "Cocktail" | 20.0 | 0 | 100+ |

The data in Table VI show that hydrocarbon emissions in engines operated on gasoline compositions containing an additive of this invention surprisingly do not appreciably increase with time as is the case with a base fuel and a fuel composition containing the commercially available additive.

EXAMPLE VIII

The hydrocarbon emission reducing properties of an additive of this invention are determined as follows. A clean CLR engine is run on a base gasoline composition containing 3 ml. of TEL/gal. until equilibrium hydrocarbon emission is reached after approximately 95 hours. The increase in hydrocarbon emission at equilibrium relative to initial hydrocarbon emission is determined (FID) and expressed in p.p.m. The engine is then switched to a leaded (3 ml. of TEL/gal.) test fuel containing an additive "cocktail" having the composition of that described in Example I and run for an additional 75 hours. The hydrocarbon emission is again determined (FID) and the difference relative to the equilibrium hydrocarbon emission is recorded, expressed in p.p.m. A + Δ hydrocarbon emission indicates an increase and a − Δ hydrocarbon emission indicates a decrease in the hydrocarbon emission. Table VII shows the concentration of the additive "cocktail" in the test fuel, the Δ hydrocarbon emission at equilibrium, and the Δ hydrocarbon emission after 75 hours of running on test fuel. Each of the three runs is made on a different CLR engine.

TABLE VII

| Concentration of Additive "Cocktail" in Test Fuel, PTB | Δ Hydrocarbon Emission at Equilibrium on Base Fuel, p.p.m. | Δ Hydrocarbon Emission After 75 Hours on Test Fuel, p.p.m. |
|---|---|---|
| 20.0 | +325 | +12 |
| 40.0 | +230 | −185 |
| 67.0 | +380 | −195 |

The data in Table VII show that when an engine running on a base leaded gasoline has reached hydrocarbon emission equilibrium, switching the engine to a leaded gasoline composition containing an additive of this invention causes only a negligible increase in hydrocarbon emission at lower additive level and, surprisingly, at higher additive levels causes a marked decrease in hydrocarbon emissions. This suggests that additives of this invention remove or alter lead deposits from engines since lead deposits are considered to be a major cause of hydrocarbon emissions in engine exhaust.

EXAMPLE IX

A 9 car fleet test is run using identical 1970 Chevrolets having 350 cubic inch displacement engines. The test involves 10,000 miles of urban-suburban consumer type driving. Three cars are run on a base gasoline containing only 3 ml. of TEL/gal.; 3 cars are run on leaded (3 ml. of TET/gal.) gasoline containing 15 PTB of DMA-4; and 3 cars are run on leaded (3 ml. of TEL/gal.) gasoline containing 20 PTB of an additive "cocktail" having the composition of that of Example I. At the end of 10,000 miles, each car is rated in the following tests:

Carburetor Rating:
The cleanliness of each carburetor is given a numerical rating on a scale of 0 to 10, with 10 being the cleanest and 0 the dirtiest.

Hydrocarbon Emission:
The hydrocarbon emission level is determined by means of nondispersive infrared (NDIR) and by means of a flame ionization detector (FID). The hydrocarbon level in the exhaust is expressed in p.p.m.

Octane Requirement Increase (ORI):
The difference in octane number requirement of each car at the end of the test relative to the octane number requirement at the start, using a full boiling range reference fuel, is determined.

Table VIII contains the results of the foregoing tests. The data for each fuel composition are the average of the data obtained from the three cars tested with that fuel.

TABLE VIII

| Gasoline Composition | Average Carburetor Rating | Average Hydrocarbon Emission, p.p.m. NDIR | Average Hydrocarbon Emission, p.p.m. FID | Octane Requirement Increase |
|---|---|---|---|---|
| Base Fuel Containing 3 ml. TEL/gal. | 3.5 | 170 | 376 | 2.2 |
| Base Fuel Containing 3 ml. TEL/gal. and 20 PTB of Additive "Cocktail" | 6.7 | 114 | 269 | 2.2 |
| Base Fuel Containing 3 ml. TEL/gal. and 15 PTB of DMA-4 | 5.5 | 173 | 365 | 3.3 |

It is seen from the data in Table VIII that engines run on a fuel composition containing a "cocktail" of an additive of this invention have cleaner carburetors and lower hydrocarbon emissions than engines run on a base fuel or a gasoline composition containing a commercially available multi-purpose additive. In addition, the octane requirement increase for engines run on the fuel composition containing the inventive additive is no more than that for engines run on base fuel and is considerably less than that for engines run on gasoline containing the commercial additive.

EXAMPLE X

Leaded (3 ml. of TEL/gal.) gasoline compositions may be prepared containing 4 PTB, 10 PTB, 30 PTB, or 50 PTB, respectively, of the mixture of isooctyl dihydrogen orthophosphate and diisooctyl hydrogen orthophosphate salts of the diamide obtained by condensing 1 mole of dimer acid with 2 moles of N-tallowyl-1,3-propylenediamine. The gasoline compositions will be found to have good carburetor detergency and carburetor anti-icing properties as well as good water tolerance and rust inhibiting characteristics. Engines run on the gasoline compositions will exhibit reduced deposit build-up and reduced hydrocarbon emissions in the exhaust.

wherein R, R', R'', $m$, and $n$ are as defined above. Each of the polyamino-polyamides can be reacted according to the procedure of Example I with a hydrocarbyl acid phosphate so that at least 10% of the amino groups in the polyaminopolyamides are converted to the hydrocarbyl acid phosphate salt. Table IX lists the various amide-forming polycarboxylic acids, the diamines, the salt-forming hydrocarbyl acid phosphates, the percent of the amino groups of the polyamino-polyamides converted to the hydrocarbyl acid phosphate salts, and the letter designation assigned to each additive product.

TABLE IX

| Polycarboxylic Acid | Diamine | Salt-Forming Hydrocarbyl Acid Phosphate | % Amino Groups Converted to Salt | Additive Product |
|---|---|---|---|---|
| succinic acid | N-oleyl-1,3-propylenediamine | triethyl hydrogen pyrophosphate | 70 | a |
| adipic acid | 1,12-diaminododecane | diphenyl hydrogen orthophosphate | 100 | b |
| terephthalic acid | N-cyclohexyl-ethylenediamine | cyclohexyl dihydrogen orthophosphate | 60 | c |
| trimer acid | ethylenediamine | methylphenyl dihydrogen pyrophosphate | 90 | d |
| pyromellitic acid | 1,4-diaminohexane | pentadecyl dihydrogen orthophosphate | 80 | e |
| 1,18-dicarboxyoctadecane | hexamethylenediamine | diphenyl hydrogen orthophosphate | 40 | f |
| glutaric acid | N,N-dibutyl-ethylenediamine | diisooctyl hydrogen orthophosphate | 100 | g |
| 1,4-cyclohexane-dicarboxylic acid | N-(10-phenylstearyl)-1,3-propylenediamine | heptyl dihydrogen orthophosphate | 10 | h |
| Versadyme 216 dimer acid | propylenediamine | triethyl hydrogen pyrophosphate | 30 | i |

EXAMPLE XI

By the procedure of Example I, various polycarboxylic acids may be condensed with various diamines so that each carboxyl group of the acid condenses with one amino group of the diamine to form the N-substituted polyamide wherein each of the substituent groups contains the unreacted amino group. The reaction is represented as follows

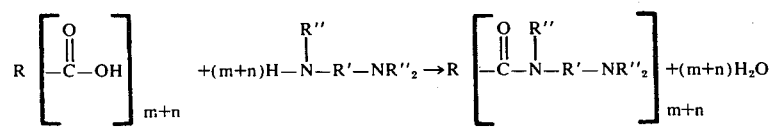

EXAMPLE XII

Several diamides are prepared by condensing 1 mole of a dicarboxylic acid with 1 mole of a monoamine whereby 1 carboxyl group is converted to the amide and the other remains unchanged. This intermediate product is reacted with 1 mole of a diamine whereby the remaining carboxyl group is condensed with 1 amino group of the diamine to yield a diamide having a amino group. The reaction is represented as follows

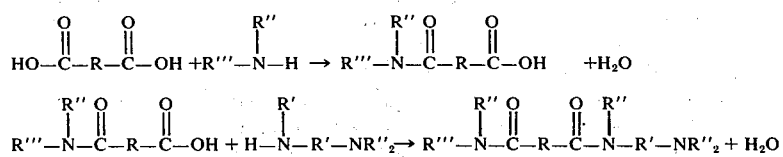

wherein R, R', R'' and R''' are as defined above. Each of the amino-diamides so formed is reacted according to the procedure of Example I with a hydrocarbyl acid phosphate so that at least 10% of the amino groups in the amino-diamide are converted to the hydrocarbyl acid phosphate salt. Table X lists the amide-forming dicarboxylic acids, the monoamines, the diamines, the salt-forming hydrocarbyl acid phosphates, the percent of the amino groups of the amino-diamides converted to the hydrocarbyl acid phosphate salts, and the letter designation assigned to each additive product.

TABLE X

| Dicarboxylic Acid | Monoamine | Diamine | Salt-Forming Hydrocarbyl Acid Phosphate | % Amino Groups Converted to Salt | Additive Product |
|---|---|---|---|---|---|
| Versadyme 216 dimer acid | diethylamine | ethylenediamine | cyclohexyl dihydrogen orthophosphate | 50 | j |
| 1,18-dicarboxy-octadecane | methylbutylamine | N-methyl-N'-propyl 1,3-propylenediamine | diisooctyl hydrogen orthophosphate | 90 | k |
| terephthalic acid | cyclohexylamine | N-oleyl-1,3-propylenediamine | isooctyl dihydrogen orthophosphate | 10 | l |
| 1,4-cyclohexane-dicarboxylic acid | propylamine | N-(10-phenylstearyl)-1,3-propylenediamine | diphenyl hydrogen orthophosphate | 100 | m |
| adipic acid | dodecylamine | N-oleyl-1,3-propylenediamine | triethyl hydrogen pyrophosphate | 75 | n |

EXAMPLE XIII

Leaded (3 ml. TEL/gal.) gasoline compositions containing the additives of this invention may be prepared by dissolving the additives in a base leaded gasoline. Such gasoline compositions may, for example, contain 500 PTB of additive $b$; 25 PTB of additive $n$; 1 PTB of additive $m$; 350 PTB of additive $l$; 45 PTB of additive $a$; 8 PTB of additive $f$; 37 PTB of additive $g$; 10 PTB of a "cocktail" containing 50 weight percent of additive $k$; 900 PTB of a "cocktail" containing 50 weight percent of additive $e$; 60 PTB of a "cocktail" containing 40 weight percent of additive $h$; 85 PTB of a "cocktail" containing 45 weight percent of additive $i$; or 7 PTB of a "cocktail" containing 45 weight percent of additive $j$. The gasoline compositions will be found to have good carburetor detergency and anti-icing properties as well as good water tolerance and rust inhibiting characteristics. In addition, engines run on these fuel compositions will exhibit reduced hydrocarbon emissions.

EXAMPLE XIV

Suitable unleaded gasoline compositions may be prepared by dissolving the additives of our invention in a base unleaded gasoline. Exemplary compositions may contain 50 PTB of additive $c$; 425 PTB of additive $i$; 4 PTB of additive $d$; 130 PTB of additive $j$; 18 PTB of additive $h$; 40 PTB of additive $k$; 27 PTB of additive $e$; 5 PTB of a "cocktail" containing 50 weight percent of additive $m$; 70 PTB of a "cocktail" containing 40 weight percent of additive $a$; 1,000 PTB of a "cocktail" containing 50 weight percent of additive $l$; 300 PTB of a "cocktail" containing 60 weight percent of additive $k$; 50 PTB of a "cocktail" containing 45 weight percent of additive $c$; or 20 PTB of a "cocktail" containing 45 weight percent of additive $b$. The gasoline compositions will have good carburetor detergency and anti-icing properties in addition to good rust inhibiting and water tolerance characteristics. Furthermore, spark ignition engines run on these fuel compositions will be characterized by lessened hydrocarbon emissions in the exhaust.

EXAMPLE XV

Diesel fuel compositions containing the additives of this invention can be prepared. Suitable compositions contain, for instance, 1 PTB of additive $b$; 35 PTB of additive $k$; 6 PTB of additive $d$; 400 PTB of additive $l$; 30 PTB of a "cocktail" containing 50 weight percent of additive $n$; 850 PTB of a "cocktail" containing 55 weight percent of additive $i$; 95 PTB of a "cocktail" containing 45 weight percent of additive $m$; 15 PTB of a "cocktail" containing 50 weight percent of additive $g$; or 60 PTB of a "cocktail" containing 45 weight percent of additive $e$. These diesel fuel compositions will be found to have good water tolerance and rust inhibiting properties. Furthermore, engines run on the above fuel compositions will have cleaner fuel intake systems than engines run on base fuel containing no additive.

EXAMPLE XVI

Jet fuel compositions can be prepared by dissolving the additives of this invention in a base jet fuel. Suitable compositions may contain 375 PTB of additive $a$; 7 PTB of additive $j$; 30 PTB of additive $c$; 2 PTB of additive $l$; 45 PTB of additive $e$; 15 PTB of a "cocktail" containing 45 weight percent of additive $j$; 900 PTB of a "cocktail" containing 50 weight percent of additive $l$; 60 PTB of a "cocktail" containing 60 weight percent of additive $h$; 6 PTB of a "cocktail" containing 40 weight percent of additive $f$; 93 PTB of a "cocktail" containing 45 weight percent of additive $b$; or 42 PTB of a "cocktail" containing 50 weight percent of additive $d$. The jet fuel compositions will be found to have good rust inhibiting properties and pass the water tolerance tests. As a result of the good water tolerance characteristics, jet fuel compositions containing the additives of this invention will not tend to pick up water. Hence there will be a reduced tendency toward ice formation and fuel filter plugging.

EXAMPLE XVII

A test to determine intake system deposit build-up is carried out. Initially clean 6 cylinder, 230 cubic inch engines are run for 115 hours under a simulated suburban driving schedule. One engine is run on a base gasoline containing 3 ml. of TEL/gal. and one engine is run on a leaded (3 ml. of TEL/gal.) gasoline containing 20 PTB of the "cocktail" described in Example I. In each case, the hydrocarbon emissions are determined (NDIR) at the start and at the end of the test. In addition, the amount of combustion chamber deposits in each engine is determined. The results of the test are given in Table XI.

TABLE XI

| | Base Fuel Containing 3 ml. TEL/gal. | Base Fuel Containing 3 ml. TEL/gal. and 20 PTB of Additive "Cocktail" |
|---|---|---|
| Hydrocarbon Emissions, p.p.m. | | |
| Start | 276 | 327 |
| Finish | 604 | 549 |
| Δ Emissions | +328 | +222 |
| Combustion Chamber | | |

TABLE XI-continued

|  | Base Fuel Containing 3 ml. TEL/gal. | Base Fuel Containing 3 ml. TEL/gal. and 20 PTB of Additive "Cocktail" |
|---|---|---|
| Deposits, g. | 40.2 | 35.8 |

The data in Table XI show the much smaller increase in hydrocarbon emissions with time for an engine run on gasoline containing a "cocktail" of the additive of this invention relative to the increase in hydrocarbon emissions for an engine run on base leaded gasoline. It is also shown that the engine run on gasoline containing our additive has reduced combustion chamber deposits.

While the invention has been described above with respect to certain preferred embodiments thereof, it will be understood by those skilled in the art that various changes and modifications may be made without departing from the spirit and scope of the invention.

We claim:

1. A composition consisting essentially of a hydrocarbyl hydrogen phosphate salt of a compound having the formula

wherein $m$ is at least 1 and the sum of $n$ plus $m$ is from 2 to about 6, R is a multivalent hydrocarbon group of about 2 to about 52 carbons, R' is a hydrocarbylene group of about 2 to about 12 carbons, R'' is selected from the group consisting of hydrogen and hydrocarbyl groups of about 1 to about 30 carbons, R''' is a hydrocarbyl group of about 2 to about 12 carbons, and at least about 10% of the amino groups contained therein are converted to the hydrocarbyl hydrogen phosphate salt wherein each hydrocarbyl group of the phosphate molecule contains from 1 to about 15 carbon atoms.

2. The composition of claim 1 wherein R is a multivalent hydrocarbon group of about 4 to about 34 carbons, R' is a hydrocarbylene group of about 2 to about 6 carbons, R'' is selected from the group consisting of hydrogen and hydrocarbyl groups of about 3 to about 24 carbons, R''' is a hydrocarbyl group of about 2 to about 6 carbons, and about 50% to about 90% of the amino groups contained therein are converted to the hydrocarbyl hydrogen phosphate salt.

3. The composition of claim 2 wherein $n$ is zero and $m$ is 2.

4. The composition of claim 2 wherein the salt-forming hydrocarbyl hydrogen phosphate is a hydrocarbyl hydrogen orthophosphate.

5. The composition of claim 3 wherein the salt-forming hydrocarbyl hydrogen phosphate is an alkyl hydrogen orthophosphate.

6. A composition consisting essentially of a hydrocarbyl hydrogen orthophosphate salt of a compound selected from the group consisting of

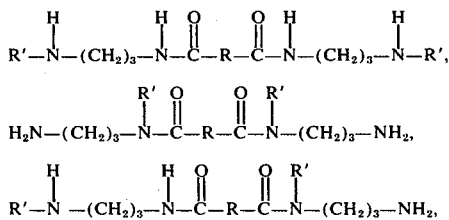

and mixtures thereof wherein R is the $C_{34}$ hydrocarbylene portion of the dimer of a polyunsaturated $C_{18}$ monocarboxylic fatty acid, R' is tallowyl, each hydrocarbyl group of the hydrocarbyl hydrogen orthophosphate contains from 1 to about 15 carbons, and about 50% to about 90% of the amino groups are converted to the hydrocarbyl hydrogen orthophosphate salt.

7. The composition of claim 6 wherein the salt-forming hydrocarbyl hydrogen orthophosphate is a mixture of isooctyl dihydrogen orthophosphate and diisooctyl hydrogen orthophosphate.

8. The composition of claim 7 wherein the salt-forming hydrocarbyl hydrogen orthophosphate comprises about 65 weight percent of diisooctyl hydrogen orthophosphate and about 35 weight percent of isooctyl dihydrogen orthophosphate.

* * * * *